(12) United States Patent
Ogilvie

(10) Patent No.: US 7,288,662 B2
(45) Date of Patent: Oct. 30, 2007

(54) PROCESS FOR THE PREPARATION OF ELETRIPTAN

(75) Inventor: Ronald James Ogilvie, County of Kent (GB)

(73) Assignee: Pfizer, Inc., New York, NY (US)

( * ) Notice: Subject to any disclaimer, the term of this patent is extended or adjusted under 35 U.S.C. 154(b) by 240 days.

(21) Appl. No.: 10/974,670

(22) Filed: Oct. 26, 2004

(65) Prior Publication Data

US 2005/0059828 A1    Mar. 17, 2005

Related U.S. Application Data

(62) Division of application No. 10/054,727, filed on Nov. 13, 2001, now abandoned.

(60) Provisional application No. 60/260,752, filed on Jan. 10, 2001.

(30) Foreign Application Priority Data

Dec. 20, 2000 (GB) ................................ 0031094.6

(51) Int. Cl.
C07D 209/04 (2006.01)

(52) U.S. Cl. ..................................... 548/465
(58) Field of Classification Search ................ 548/465
See application file for complete search history.

(56) References Cited

U.S. PATENT DOCUMENTS 5,545,644 A * 8/1996 Macor et al. ............... 514/323
5,607,951 A    3/1997 Macor et al.
6,110,940 A    8/2000 Harding et al.

FOREIGN PATENT DOCUMENTS

EP          0 592 438 B1   8/1997
WO     WO 1992/06973 A1   4/1992

OTHER PUBLICATIONS

Kojima, wt al., "Fluorescent Properties of Model Chromophores of Tyrosine-66 Substituted Mutants of Aequorea Green Fluorescent Protein", Tetrahedron Letters, 1998, pp. 5239-5242, vol. 39, No. 29.
Willems, et al., "Porcine Carotid Vascular Effects of Eletriptan (UK-0116,044): A New 5-HT1b/1D Receptor Agonist with Anti-Migraine Activity", Naunyn-Scmiedeberg's Arch Pharmacology, 1998, pp. 212-219, vol. 358, No. 2.

* cited by examiner

Primary Examiner—Johann Richter
Assistant Examiner—Ebenezer Sackey
(74) Attorney, Agent, or Firm—Philip B. Polster, II

(57) ABSTRACT

The present invention provides an improved process for the preparation of the anti-migraine drug, (R)-5-(2-benzene-sulphonylethyl)-3-N-methylpyrrolidin-2-ylmethyl)-1H-indole (eletriptan), available commercially as the hydrobromide salt, and an intermediate and dimer-free products obtained from such process.

3 Claims, No Drawings

PROCESS FOR THE PREPARATION OF ELETRIPTAN

This application is a divisional of Ser. No. 10/054,727, filed Nov. 13, 2001 now abandoned, which claims the benefit of provisional application Ser. No. 60/260,752, filed Jan. 10, 2001.

The present invention is concerned with an improved process for the preparation of the anti-migraine drug, (R)-5-(2-benzenesulphonylethyl)-3-N-methylpyrrolidin-2-ylmethyl)-1H-indole (eletriptan), available commercially as the hydrobromide salt:

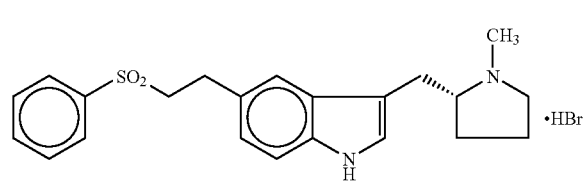

and with an intermediate and dimer-free products obtained thereby.

European Patent No. 0592438 describes the preparation of eletriptan by the catalytic reduction of (R)-5-(2-benzenesulphonylethenyl)-3-(N-methylpyrrolidin-2-ylmethyl)-1H-indole, which compound is prepared by (i) reacting N-benzyloxycarbonyl-D-proline acid chloride with 5-bromoindole in the presence of a Grignard reagent, (ii) reducing the resulting (R)-3-(N-benzyloxycarbonylpyrrolidin-2-ylcarbonyl)-5-bromo-1H-indole to give (R)-5-bromo-3-(N-methylpyrrolidin-2-ylmethyl)-1H-indole and (iii) reacting same with phenyl vinyl sulphone in the presence of a palladium catalyst, a triarylphosphine and a base.

The complete sequence may be represented as follows:

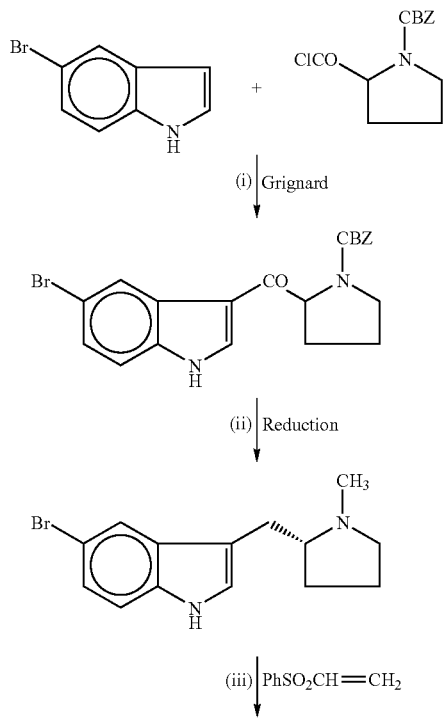

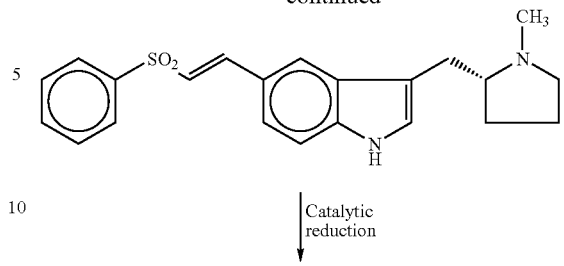

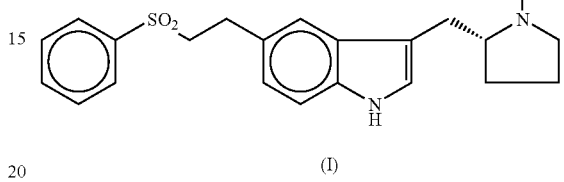

(I)

While the foregoing sequence produces eletriptan of formula (I) in reasonable yield, it has been found that the (R)-5-(2-benzenesulphonylethenyl)-3-(N-methylpyrrolidin-2-ylmethyl)-1H-indole precursor is prone to dimerise when attempting to recrystallise in impure form and/or drying prior to catalytic reduction:

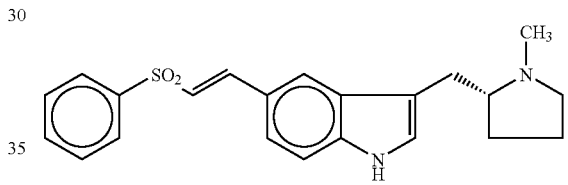

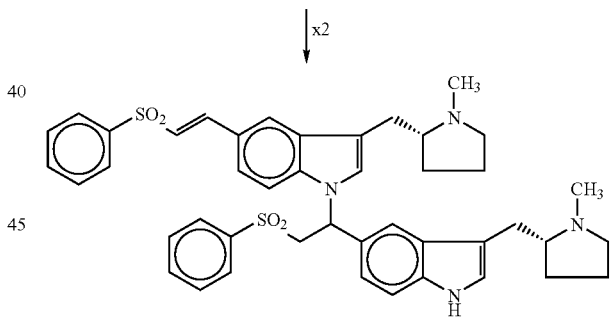

Not only does the formation of this dimeric impurity reduce the yield of eletriptan, but, perhaps more importantly, it requires the costly and time-consuming removal of said dimer in order to provide hydrobromide salt of sufficient purity to meet the stringent standards required for regulatory approval.

As a result of this difficulty, we have now developed an alternative route to eletriptan which avoids the use of a precursor which is prone to dimerisation. Specifically, the process of the invention comprises the preparation of eletriptan by the hydrolysis of (R)1-acetyl-5-(2-benzenesulphonylethyl)-3-(N-methylpyrrolidin-2-ylmethyl)-1H-indole, which compound may conveniently be prepared by (i) N-acetylating (R)-5-bromo-3-(N-methylpyrrolidin-2-ylmethyl)-1H-indole, (ii) reacting the resulting (R)-1-acetyl-5-bromo-3-(N-methylpyrrolidin-2-ylmethyl)-1H-indole with phenyl vinyl sulphone in the presence of a palladium catalyst, a triarylphosphine and a base to give (R)-1-acetyl-5-(2-benzenesulphonylethenyl)-3-(N-methylpyrrolidin-2-yl-methyl)-1H-indole and (iii) catalytically reducing same.

The complete sequence may be represented as follows:

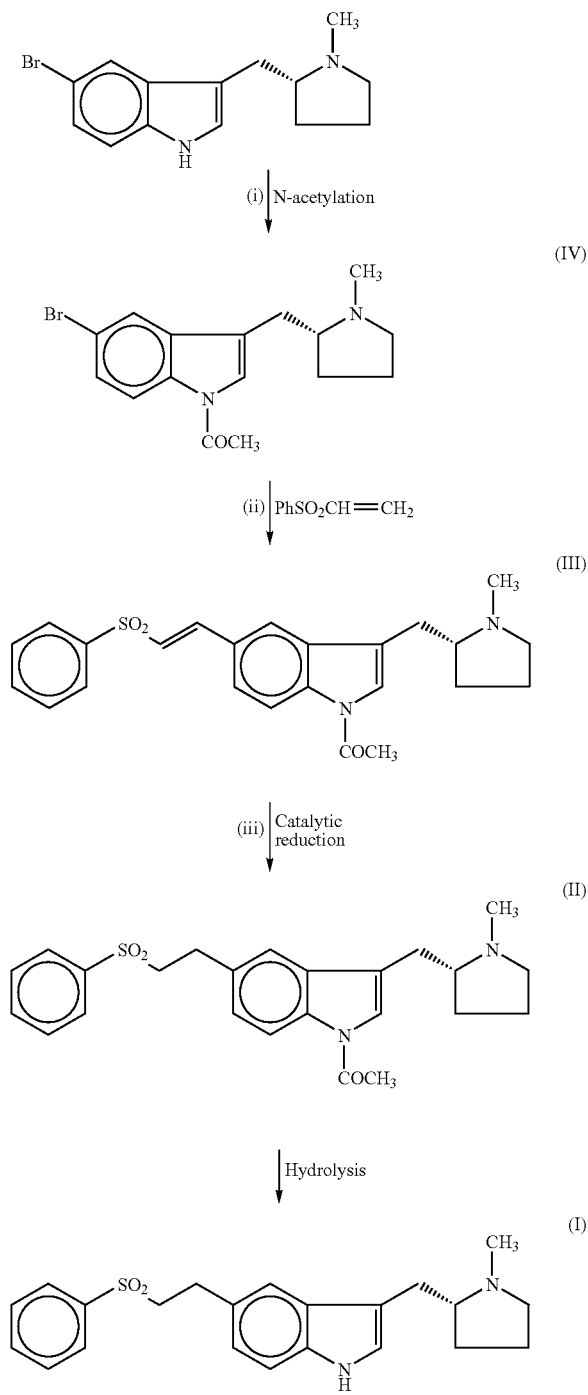

By the use of this process, it is possible to avoid the formation of unwanted dimer and thereby obtain eletriptan of high purity in good yield without the subsequent costly and time-consuming purification steps needed to remove the dimeric impurity. Thus according to the present invention, there is provided a process for the preparation of a compound of formula (I) which comprises hydrolysis of a compound of formula (II), typically under basic conditions, more especially potassium carbonate in methanol/water.

According to another aspect of the invention, the compound of formula (II) used in the process may be obtained by catalytic reduction of a compound of formula (III), typically using hydrogen or a hydrogen source in the presence of a suitable catalyst. The reduction is typically carried out using hydrogen at a pressure of from 1 to 15 atmospheres or using a hydrogen source such as ammonium formate or formic acid. Suitable catalysts include palladium on carbon, for example, 5% w/w Pd/C, Raney nickel, platinum oxide, rhodium, or ruthenium. The reduction is conveniently carried out in the presence of an acid, for example, methanesulphonic acid, acetic acid, or trifluoroacetic acid. The compound of formula (II) so obtained is conveniently slurried with cold aqueous tetrahydrofuran before hydrolysis to the compound of formula (I).

The invention specifically provides the aforementioned compound of formula (II) which has not hitherto been described.

According to yet another aspect of the invention, the compound of formula (III) used in the process may be obtained by treating a compound of formula (IV) with phenyl vinyl sulphone in the presence of a palladium catalyst, a triarylphosphine and a base in accordance with the process described in Example 57 of U.S. Pat. No. 5,607,951.

According to yet a further aspect of the invention, the compound of formula (IV) used in the process may be obtained by the N-acetylation of (R)-5-bromo-3-(N-methylpyrrolidin-2-ylmethyl)-1H-indole, also in accordance with the process described in Example 57 of aforementioned U.S. Pat. No. 5,607,951.

Eletriptan obtained by the process of the invention may be converted to a pharmaceutically acceptable acid addition salt by treatment with an appropriate acid; said conversion may conveniently be carried out in situ without isolation of the compound of formula (I). A particularly preferred salt is the hydrobromide obtained by treatment with hydrobromic acid.

Thus according to the present invention, there is also provided dimer-free eletriptan and pharmaceutically acceptable salts thereof, particularly the hydrobromide, and pharmaceutical compositions comprising same.

EXAMPLE

The process of the invention may be illustrated by the following example of the preparation of (R)-5-(2-benzenesulphonylethyl)-3-N-methylpyrrolidin-2-ylmethyl)-1H-indole (I) and its hydrobromide salt:

(a) Preparation of (R)-1-acetyl-5-(2-benzenesulphonylethyl)-3-(N-methylpyrrolidin-2-ylmethyl)-1H-indole (II)

To a solution of the compound of formula (III) (200 g) prepared by the method described in Example 57 of aforementioned U.S. Pat. No. 5,607,951 in acetone (2.0 L) was added water (0.5 L). Methanesulphonic acid (43.2 g, 0.95 equiv.) was added dropwise and the resulting solution stirred for 5 minutes before adding 5% w/w Pd/C catalyst (89.0 g, Johnson Mattey Type 58, 50% wet). The solution was hydrogenated at room temperature at 200 psi hydrogen for 18 hours.

The catalyst was removed by filtration and the filtrate stripped to give an acetone-free slurry. To this was added dropwise 40% aqu. NaOH (30mL) followed by water (1.5 L). The resulting slurry was stirred for 20 minutes and further 40% aqu. NaOH (20 mL) added. After granulation for 2 hours under vigorous stirring, the suspension was filtered and sucked dry for 30 minutes to give a beige damp solid which was either (i) dried at 45° C. to give the desired product (193.0 g, yield 95%) or (ii) taken up in tetrahydrofuran (1.6 L) to which was added water (1.5 L in total) over 10 minutes. The resulting suspension was stirred vigorously for 18 hours, filtered and sucked dry for 30 minutes to give the desired product as a beige damp solid (corrected weight 129.0 g, yield 67%).

Either form may be used directly in step (b):

(b) Preparation of (R)-5-(2-benzenesulphonylethyl)-3-N-methylpyrrolidin-2-ylmethyl)-1H-indole (I)

To a solution of the compound of formula (II) (95.9 g) from step (a)(i) or (ii) in acetone (1 L) and methanol (0.1 L) was added $K_2CO_3$ (46.8 g, 1.5 equiv.) and the resulting mixture stirred for 24 hours. To this was added charcoal (50 g) followed an hour later by any. $MgSO_4$ (300 g). The resulting suspension was stirred for 1 hour and filtered. The filtrate was stripped to give a damp solid which was dried in vacuo at 45° C. to give the desired product (79.3 g, 91.8%).

In the case where the compound of formula (I) is to be converted to a pharmaceutically acceptable acid addition salt, isolation of the compound of formula (I) may be avoided by directly treating the solution obtained by hydrolysis with the appropriate acid, for example, hydrobromic acid to give the hydrobromide salt:

(c) Preparation of (R)-5-(2-benzenesulphonylethyl)-3-N-methylpyrrolidin-2-ylmethyl)-1H-indole (I) and in situ hydrobromination thereof To a solution of the compound of formula (II) (95.9 g) from step (a)(i) or (ii) in acetone (1 L) and methanol (0.1 L). was added $K_2CO_3$ (46.8 g, 1.5 equiv.) and the resulting mixture stirred for 24 hours. To this was added charcoal (50 g) followed an hour later by anhy. $MgSO_4$ (300 g). The resulting suspension was stirred for 1 hour and filtered.

The filtrate was partially concentrated by azeotropic distillation to remove methanol and the volume readjusted to 0.45 L with acetone. A solution of 48% w/v HBr (33.2 g, 0.95 equiv.) in acetone (50 mL) was added dropwise and the resulting suspension stirred for 72 hours. This was filtered, sucked dry for 30 minutes and dried in vacuo at 45° C. to give the desired product as slightly beige crystals (71.8 g, 68.5%).

In a preferred embodiment of the invention, certain steps may be 'telescoped' in order to reduce handling and accelerate processing time. For example, as indicated in step (a)(ii), drying the compound of formula (II) prior to hydrolysis may be avoided by using damp material slurried in aqueous tetrahydrofuran. Likewise, as indicated in step (c), isolation of the compound of formula (I) before conversion to a salt may be avoided by forming the salt in situ.

The invention claimed is:

1. A process for the preparation of a compound of formula (I)

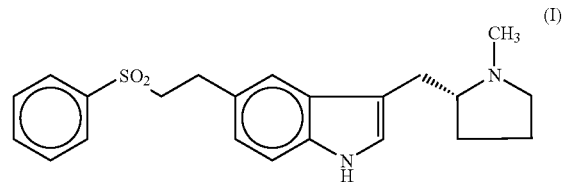

which comprises hydrolysis of a compound of formula (II)

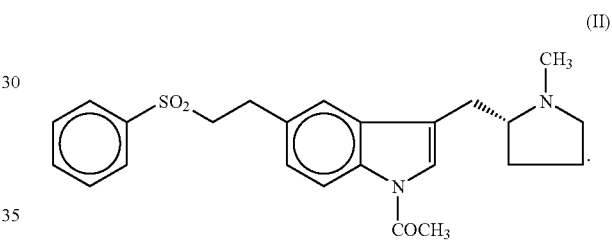

2. A process according to claim 1 which is carried out under basic conditions.

3. A process according to claim 2 wherein said hydrolysis is performed using potassium carbonate in methanol/water.

* * * * *